United States Patent [19]

Toriu et al.

[11] Patent Number: 4,949,721
[45] Date of Patent: Aug. 21, 1990

[54] TRANSCUTANEOUS ELECTRIC NERVE STIMULATER

[75] Inventors: Mamoru Toriu, Sayama; Ikuo Onishi, Tokyo; Youichiro Tani, Warabi; Nobuo Ogiwara, Machida; Hiroshi Tanikoshi, Tokyo; Mitsuru Kitamura, Yokohama, all of Japan

[73] Assignees: Omron Tateisi Electronics co., Kyoto; Ito Co., Ltd., Tokyo, both of Japan

[21] Appl. No.: 389,582

[22] Filed: Aug. 4, 1989

[30] Foreign Application Priority Data

Aug. 11, 1988 [JP] Japan .................................. 63-200596
Aug. 11, 1988 [JP] Japan ........................... 63-106500[U]

[51] Int. Cl.$^5$ ............................................. A61N 1/00
[52] U.S. Cl. .................................... 128/421; 128/422; 128/419 R
[58] Field of Search ............ 128/421, 422, 783, 419 R

[56] References Cited

U.S. PATENT DOCUMENTS

| 4,154,240 | 5/1979 | Ikuno et al. | 128/422 |
| 4,556,064 | 12/1985 | Pomeranz et al. | 128/395 |
| 4,573,449 | 3/1986 | Warnke | 128/422 |
| 4,769,881 | 9/1988 | Pedigo et al. | 128/421 |

Primary Examiner—Francis Jaworski
Assistant Examiner—George Manuel
Attorney, Agent, or Firm—Wegner & Bretschneider

[57] ABSTRACT

In a transcutaneous electric nerve stimulater in which a frequency of an output pulse varies with a lapse of time, a pulse width of the output pulse is increased when the frequency becomes to be smaller and is reduced when the frequency becomes to be greater. Furthermore, a pulse amplitude of the output pulse is increased when the frequency becomes to be smaller and is minimized when the frequency becomes to be greater.

8 Claims, 4 Drawing Sheets

TRANSCUTANEOUS ELECTRIC NERVE STIMULATER

BACKGROUND OF THE INVENTION

1. Field of the Invention

The present invention relates to a transcutaneous electric nerve stimulater for conducting a treatment on a stiffness, a paralysis, a pain, and the like by use of low-frequency signals.

2. Description of the Prior Art

In the prior art, there has been conducted a treatment in which a transcutaneous electric nerve stimulater is used to apply low-frequency pulses onto a human body so as to alleviate a stiffness, a paralysis, a pain, and the like of the body.

In order to effect an efficient treatment depending on a condition of the patient, such a transcutaneous electric nerve stimulater is provided with several operation modes. In one or more operation modes, the stimulater achieves an operation to repeatedly effect a sweeping operation of the frequency of the output pulses from a low frequency to a high frequency and an operation to change the frequency to a different discrete value, for example, form 1 Hz to 10 Hz. For this purpose, the transcutaneous electric nerve stimulater has a function to vary the frequency of the ouptut pulse.

In general, the function above is achieved such that a memory is disposed in the stimulater so as to beforehand store therein discrete values of frequency data such as 1 Hz, 10 Hz, 50 Hz, etc. According to a predetermined program, a frequency data item is read out form the memory so as to control an output level (high level or low level) to generate a pulse of a frequency corresponding to the data item, thereby changing the frequency of the output pulse. Incidentally, the method of changing the frequency of the output pulse by use of the frequency data stored in a memory is called a stored program control.

Incidentally, when a frequency of an output pulse applied to a human body is varied with a pulse width or amplitude kept unchanged, it has been known that a feeling of an electric shock on the human body generally decreases in a lower-frequency range and increases in a higher-frequency range.

This phenomenon also appears in the conventional transcutaneous electric nerve stimulater, which leads to a disadvantage that a uniform feeling of the electric shock is not obtained when the frequency of the output pulse is varied from a low frequency to a high frequency. In particular, when the frequency is discretely altered so as to jump from 1 Hz to 10 Hz, the electric shock on a human body greatly varies. In consequence, it is necessary to manually adjust the output level when the frequency is varied and hence there cnnot be attained a satisfactory practicability of the stimulater.

In addition, the transcutaneous electric nerve stimulater is provided in some cases with a function to invert a polarity of the output pulse inadition to the frequency change function. The polarity inverting function to invert the output pulse is included in a particular operation mode of the stimulater. The inversion of the output pulse is achieved in many cases at a point of time when the frequency of the output pulse is changed or at an arbitrary point (where a pulse to invert the polarity is to be outputted).

In the transcutaneous electric nerve stimulater of the prior art, when the frequency of the output pulse is varied or when the polarity thereof is reversed, an ouptut pulse is produced with a level identical to a level of the output pulse prior to the frequency change or the polarity inversion, which in consequence leads to a problem that the feeling of the electric shock is considerably increased.

SUMMARY OF THE INVENTION

It is therefore an object of the present invention to provide a transcutaneous electric nerve stimulater in which even when the frequency of the output pulse is varied, a uniform feeling of an electric shock is obtained, thereby solving the problem of the prior art.

Another object of the present invention is to provide a transcutaneous electric nerve stimulater in which when the frequency of the output pulse is changed or when the polarity of the output pulse is inverted, a soft feeling of an electric shock is obtained.

In order to achieve the objects above, according to the present invention, there is provided a transcutaneous electric nerve stimulater including pulse width control means which increases the pulse width of the output when the frequency thereof is reduced and which decreases the pulse width of the output pulse when the frequency thereof is increased.

In addition, the transcutaneous electric nerve stimulater according to the present invention comprises pulse amplitude control means which increases the amplitude of the output pulse when the frequency thereof is reduced and which decreases the amplitude of the output pulse when the frequency thereof is increased.

The transcutaneous electric nerve stimulater may be provided with both of or either one of the pulse width control means and the pulse amplitude control means.

The pulse width of the output pulse is controlled by the pulse width control means such that when the frequency of the output pulse is lowered, the pulse width thereof becomes to be greater; conversely, when the frequency is increased, the pulse width of the output pulse becomes to be smaller.

In the control operation achieved by the pulse amplitude control means on the output pulse amplitude, when the frequency of the output pulse is decrease, the pulse amplitude thereof becomes to be greater; conversely, when the frequency becomes to be greater, the pulse amplitude of the output pulse is decreased.

As a result, even when the frequency of the pulse is altered from a low frequency to a high frequency, a feeling of the electric shock caused by the pulse on the human body is set to be uniform.

In order to achieve the objects above, the transcutaneous electric nerve stimulater according to the present invention is characterized by including output level control menas which lowers the output level of the output pulse to a level equal to or a level in the proximity of zero immediately before when the frequency of the output pulse is changed or when the polarity thereof is inverted and which gradually increases the output level of the output pulse, immediately after the output pulse frequency change or the output pulse polarity inversion, to a level developed immediately before the output pulse frequency change or the output pulse polarity inversion or to a level related to a frequency after the frequency change or the polarity inversion.

The transcutaneous electric nerve stimulater may further includes the pulse width control means and/or the pulse amplitude control means.

In the configuration above, immediately prior to the change of the frequency of the output pulse or the inversion of the polarity thereof, the output level of the pulse is set to zero or to a level in the proximity of zero; thereafter, immediately after the frequency change or the polarity inversion, the output level of the poulse gradually increases with a lapse of time. As a result, at the frequency change or the polarity inversion of the pulse, the great electric shock of the prior art stimulater is removed and hence the feeling of the electric shock is further improved.

BRIEF DESCRIPTION OF THE DRAWINGS

These and other objects and advantages of the present invention will become apparent by reference to the following description and accompanying drawings wherein.

DESCRIPTION OF THE PREFERRED EMBODIMENT

Figure 1:
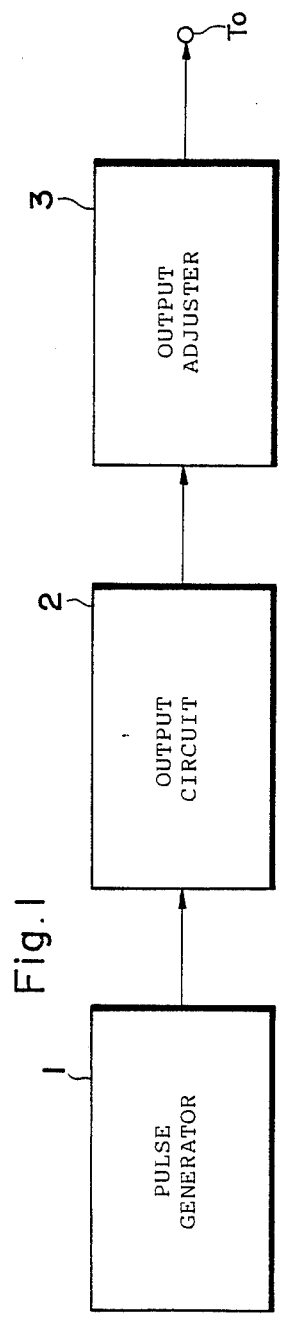
FIG. 1 is a functional block diagram showing a first embodiment according to the present invention.

Referring now to the drawings, description will be given of embodiments according to the present invention.

FIG. 1 is a functional block diagram showing a first embodiment of a transcutaneous electric nerve stimulater according to the present invention.

Figure 2:
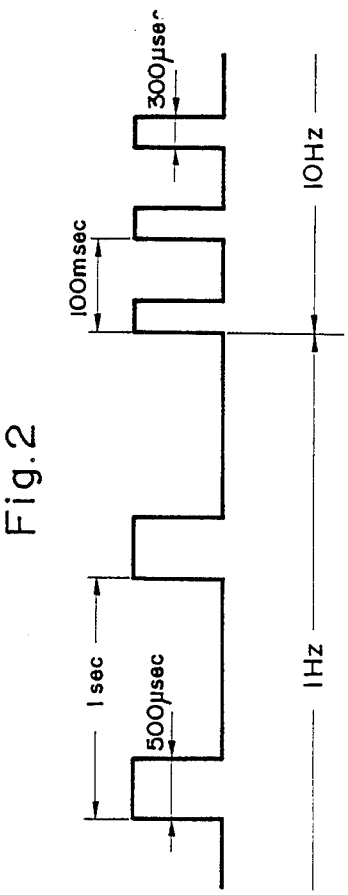
FIG. 2 is a graph useful to explain the operation of the embodiment of FIG. 1.

The configuration of FIG. 1 includes a pulse generator 1 having a central processing unit (CPU), a read-only memory (ROM), and a random access memory (RAM), which are not shown. In the ROM, there is stored a program to control the CPU, whereas the RAM is disposed to store therein pulse width data items corresponding to a plurality of frequencies in a low frequency band. For example, as shown in FIG. 2, the RAM is loaded with pulse width data items 500 microseconds ($\mu$s) and 300 $\mu$s in association with frequencies 1 Hz and 10 Hz, respectively. As can be seen from FIG. 2, the pulse width data items are stored for each frequency in the RAM such that the pulse width becomes to be greater for the lower frequency; conversely, the pulse width decreases for the higher frequency. The values of the pulse width are beforehand determined through an experiment or the like so that the feeling of the electric shock on the human body is uniform for the respective frequencies.

The CPU in the pulse generator 1 reads out, when outputting a pulse with a specified frequency, a pulse width data item related to the frequency from the RAM so as to conduct a change-over between levels (H and L levels) of the output signal (pulse) to produce a pulse having the pulse width. For the level change-over, the pulse width is computed by use of a counter or a timer such that the change-over operation is achieved depending on a count end signal produced from the counter or the timer.

The configuration further includes an output circuit 2 and an output adjuster 3 in which the output circuit 2 is employed to amplify an output pulse supplied from the pulse generator 1, whereas the output adjuster 3 is disposed to adjust, in association with, for example, a rotary angle of a manual control, a level (peak value) of a pulse supplied from the output circuit 2. The output adjuster 3 produces a pulse, which is fed via an output terminal To to electrodes, not shown.

In the transcutaneous electric nerve stimulater thus constituted, when the operator turns a power switch, not shown, on and selects a desired operation mode, the system selects and executes a program associated with the mode. According to the execution of the program, pulse width data items are sequentially read from the RAM of the pulse generator 1 such that pulses corresponding to these data items are sequentially fed to the output circuit 2. Each of the pulses supplied to the output circuit 2 is amplified to a predetermined level therein and is then delivered to the output adjuster 3, which in turn adjusts the level of the received pulse to a level desired by the operator so as to supply the resultant pulse to the electrodes, not shown.

As described above, since the pulse width of the output pulse increases when the frequency becomes to be smaller and vice versa, a uniform electric shock is obtained in a frequency range from a low frequency to a high frequency. In addition, as shown in FIG. 2, since the pulse widths are determined such that a uniform feeling of electric shock is attained for the respective frequencies, even when the frequency is abruptly varied from 1 Hz to 10 Hz, the feeling of electric shock is uniformly changed. This means that even in a case where the frequency is changed (including a case where the frequency automatically changes depending on the operation mode set by the operator and a case where the operator sets a desired frequency), the operator need not adjust the setting of the output adjuster 3, which hence greatly improves the practicability of the stimulater.

Figure 3:
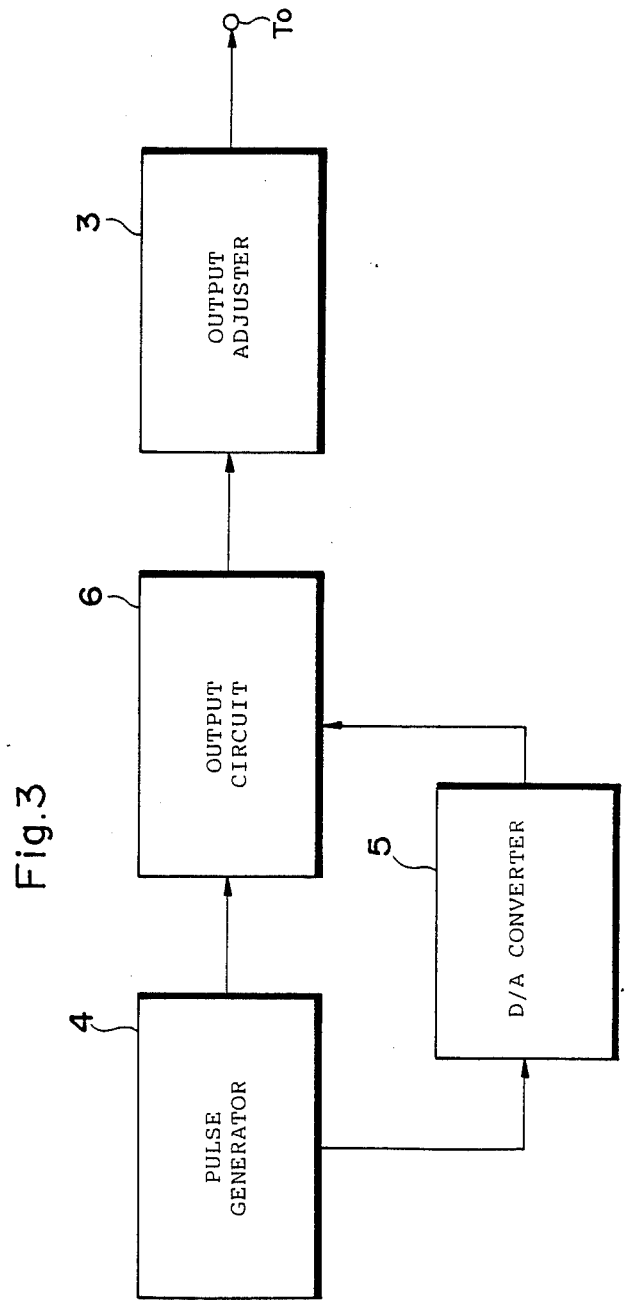
FIG. 3 is a functional block diagram showing a second embodiment according to the present invention.

Referring next to FIG. 3, description will be given of the second embodiment according to the present invention.

The configuration includes a pulse generator 4, which comprises, like in the case of the pulse generator 1 of FIG. 1, a CPU, an ROM, and an RAM. The ROM is disposed to be loaded with a program to control the CPU, whereas the RAM is used to store therein data items, which are employed to produce output pulses having amplitudes corresponding to frequencies, respectively. That is, the RAM contains data items representing the amplitudes corresponding to a plurality of different frequencies. The CPU of the pulse generator 4 is operated according to the program written in the ROM so as to create a pulse which has a fixed pulse width and of which the frequency changes with a lapse of time; furthermore, the CPU reads an amplitude data item associated with the frequency of an output pulse from the RAM so as to deliver the data item to a digital-to-analog (D/A) converter 5. The amplitude data items are beforehand produced such that the values thereof are increased when the frequency becomes to be smaller and vice versa.

The CPU of the pulse generator 4 creates a pulse to be supplied to an output circuit 6, whereas the amplitude data item is fed to the D/A converter 5, which produces a voltage proportional to the amplitude data item thus received so as to deliver the voltage to the output circuit 6. The output circit 6 amplifies the output pulse such that an amplitude of the pulse supplied from the pulse generator 4 is set to a level associated with the value of the voltage received from the D/A converter 5.

In the transcutaneous electric nerve stimulator configured as descrived above, when the operator sets a power switch, not shown, to ON and selects an operation mode in which the frequency of the output pulse is changed, the pulse generator 4 supplies the output circuit 6 with a pulse having a fixed pulse width. At the same time, the amplitude data item is supplied from the pulse generator 4 to the D/A converter 5, which in turn creates a voltage proportional to the amplitude data item and then feeds the voltage to the output circuit 6. The pulse with the fixed pulse width supplied to the output circuit 6 is amplified therein such that the pulse amplitude is proportional to the input voltage value from the D/A converter 5 so as to be delivered to the output adjuster 3. The output pulse is then adjusted in the output adjuster 3 to a level desired by the operator. The resultant signal is supplied to the electrodes, not shown.

As described above, since the output pulse amplitude increases when the frequency of the output pulse becomes to be smaller and vice versa, a uniform feeling of electric shock is attained in a frequency range from a low frequency to a high frequency.

Incidentally, in the embodiment above, the frequency of the output pulse is changed from a low frequency to a high frequency; however, the present invention is not restricted by this embodiment. For example, it may also be possible to alternately produce a pulse of a high frequency and a pulse of a low frequency.

Since the apparatus is configured as described above according to the present invention, there are obtained effects as follows.

The pulse width of the output pulse increases when the frequency thereof becomes to be smaller and vice versa or the amplitude of the output pulse becomes to be greater when the frequency thereof is decreased and vice versa; in cnsequence, even when the frequency of the output pulse is varied from a low frequency to a high frequency, there is developed a uniform feeling of electric shock on a human body. This leads to an advantage that even when the variation ratio of the frequency is increased, it is not required to adjust the output level by use of an output adjuster.

It may naturally be possible to simultaneously accomplish the pulse width control and the pulse amplitude control when the frequency of the output pulse is changed.

Figure 4:
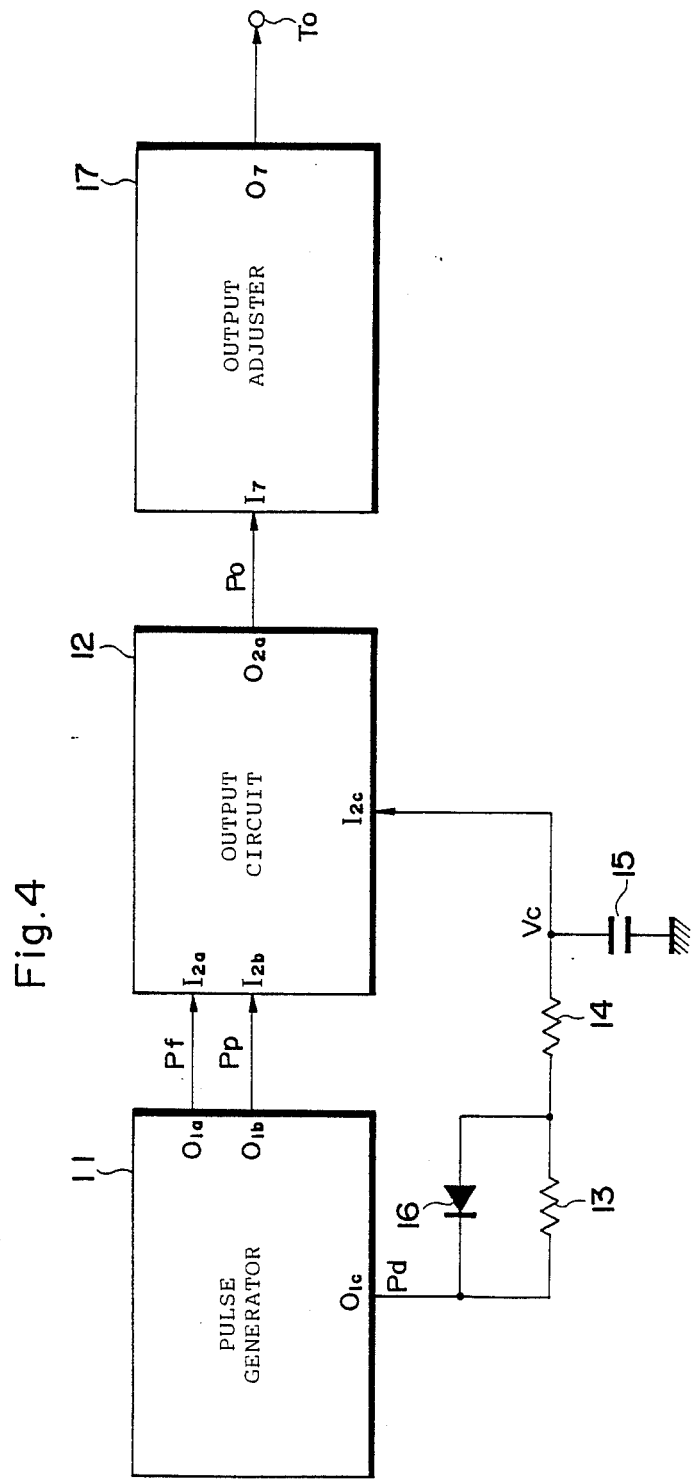
FIG. 4 is a functional block diagram showing a third embodiment according to the present invention.
Figure 5:
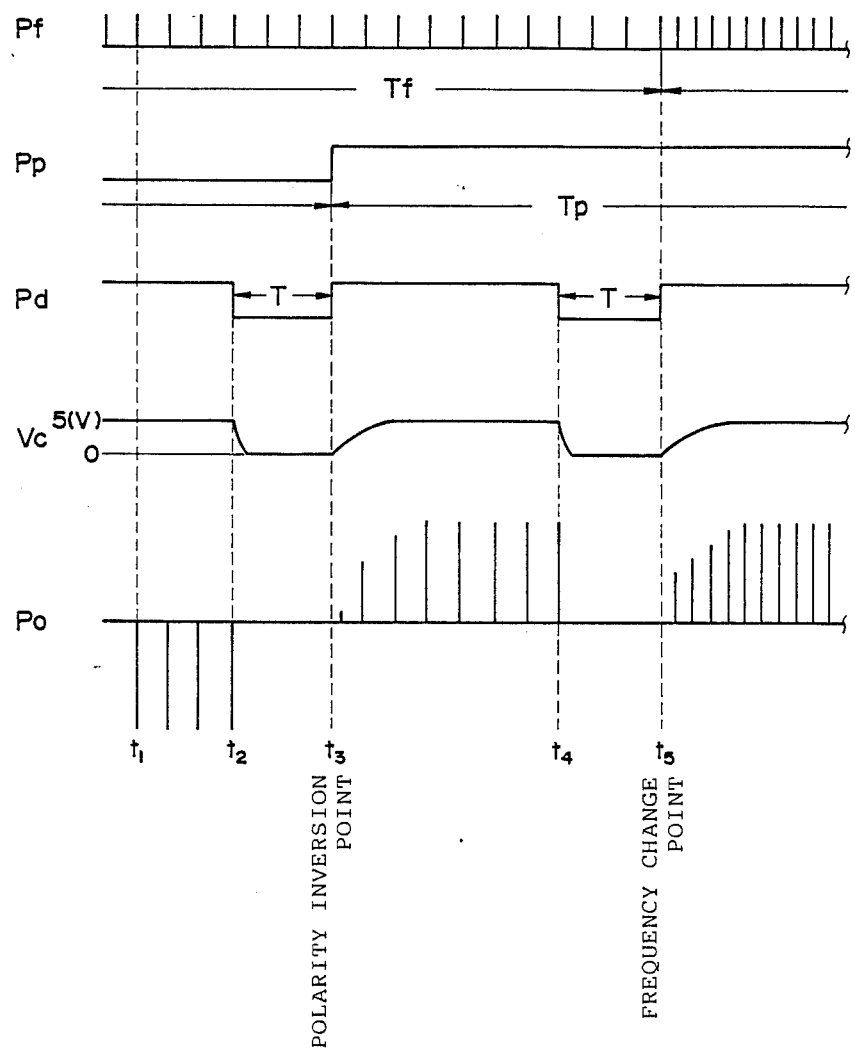
FIG. 5 is a graph useful to explain the operation of the third embodiment of FIG. 4.

FIG. 4 is a functional block diagram showing the third embodiment according to the present invention, whereas FIG. 5 is a signal timing chart showing the operation of the third embodiment. The configuration comprises a pulse generator 11 having a CPU, an ROM, and an RAM, which are not shown. The ROM is used to be loaded with a program to control the CPU, which consequently operates according to a program of a particular mode so as to generate a pulse Pf of which the frequency is changed at a period Tf having a fixed pulse width and a constant amplitude. The generated puls Pf is delivered from an output terminal $O_{1a}$ to an output circuit 12. Moreover, the CPU produces a polarity pulse Pp of which the binary logic level is inverted at a period Tp (Tp>Tf). The polarity pulse Pp is supplied from an output terminal $O_{1b}$ to the output circuit 12. Furthermore, each time the frequency of the pulse Pf is varied or each time the binary logic level of the polarity pulse Pd which changed, the CPU produces an output down pulse Pd which retains an "L" level for a fixed interval T immediately before the polarity inversion or the frequency change (an "H" level is held in other period of time). The output down pulse Pd is delivered from an output terminal $O_{1c}$.

The output circuit 12 receives via an input terminal $I_{2a}$ the pulse Pf supplied from the pulse generator 11 so as to amplify the pulse Pf and supplies the amplified signal as an output pulse Po via an output terminal $O_{2a}$ to an output adjuster 17. In this situation, an amplification ratio for amplifying the pulse Pf is varied depending of a level of a signal supplied to an input terminal $I_{2c}$. That is, when the level of the signal supplied to the input terminal $I_{2c}$ becomes smaller, the amplification ratio is decreased and vice versa.

Furthermore, the output circuit 12 receives via an input terminla $I_{2b}$ the polarity pulse Pp supplied from the pulse generator 11 so as to invert the polarity of the output pulse Po depending on the binary logic level of the polarity pulse Pp. That is, when the polarity pulse Pp is at the "L" level, the output pulse Po is produced with a negative polarity; whereas when the polarity pulse Pp is at the "H" level, the output pulse Po is generated with a positive polarity.

The output pulse Po thus undergone the amplification and the polarity setting is delivered via the output terminal $O_{2a}$ to the output adjuster 17. The output adjuster 17 is disposed to adjust, depending on a position of a control operated by the operator, the level (peak value) of the pulse Po supplied from the output circuit 12. The resultant pulse is fed from the output adjuster 17 via a terminal To to an electrode section, not shown. The low-frequency pulse is applied therefrom to a human body.

Between the output terminal $O_{1c}$ of the pulse generator 11 and the input terminal $I_{2c}$ of the output circuit 12, there is inserted an integration circuit comprising resistors 13 and 14 and a capacitor 15. Between a point where the resistors 13 and 14 are connected and the output terminal $O_{1c}$ of the pulse generator 11, there is connected a diode 16 with a cathode thereof oriented toward the output terminal $O_{1c}$ of the pulse generator 11. Assuming the values of the resistors 13 and 14 to be represented as $R_{13}$ and $R_{14}$, the system is established to hold a relationship $R_{13} >> R_{14}$. Under this condition, it is possible to discharge rapidly the capacitor 15 when the output down pulse Pd delivered from the pulse generator 11 is set to the "L" level. That is, since the electric charge stored in the capcitor 15 is discharged via the resistor 14 and diode 16, when the value $R_{14}$ of the registor 14 is set to be sufficiently smaller than the value $R_{13}$ of the registor 13, the electric charge of the capacitor 15 can be rapidly discharged. Conversely, when the capacitor 15 is charged with the electricity, the charging current flows through the registors 13 and 14; consequently, the charging operation is gradually achieved.

Referring to the wafeforms of FIG. 5, description will be given of the operation of the transcuteneous electric nerve stimulater thus constituted. Incidentally, in the following description, it is assumed that as shown in FIG. 5, at time $t_1$. The pulse Pf is being produced, that the polarity pulse Pp is at the "L" level, that the output down pulse Pd is at the "H" level, and that the voltage Vc developed between the terminals of the capacitor 15 is five volt. Since the polarity pulse is at the "L" level, the output pulse Po is produced with a negative polarity.

At time $t_2$, the pulse generator 11 alters the state such that the output down pulse Pd is changed from the "H" level to the "L" level. In this state, the electric charge stored in the capacitor 15 is rapidly discharged through the resistor 14 and the diode 16, thereby setting the voltage Vc between the ends of the capacitor 15 to 0 volt. When a period of time T is elapsed after the output down pulse Pd is set to the "L" level, namely, at time $t_3$, the pulse generator 11 changes the level of the polarity pulse $P_p$ to the "H" level and then returns the output down pulse Pd to the "H" level. Under this condition, a charge current flows via the resistors 13 and 14 to the capacitor 15; consequently, the voltage Vc between the ends of the capacitor 15 gradually increases. Since the level of the output pulse Po produced from the output circuit 12 is proportional to value of the voltage Vc, the level of Po increases when the voltage Vc becomes greater. That is, after the polarlity is inverted, the value of the output pulse Po gradually increases beginning from the zero level.

Thereafter, at time $t_4$ after the output circuit 12 produces the pulse Po with a positive polarity, the pulse generator 11 changes the state of the output down pulse Pd from the "H" level to the "L" level. In this situation, the electric charge accumulated in the capacitor 15 is discharged through the resistor 14 and the diode 16 at a high speed. At time $t_5$ when a period of time T is elapsed after the output down pulse Pd is set to the "L" level, the pulse generator 11 varies the frequency of the pulse Pf and restores the output down pulse Pd from the "L" level to the "H" level. In this state, since the capacitor 15 is gradually charged with electricity, the level of the output pulse Po gradually increases. Since the polarity pulse Pp is kept remained at the "H" level in this case, the output circuit 12 produces the output pulse Po with the positive polarity kept unchanged.

As described above, immediately before the level of the polarity pulse Pp is inverted or the frequency of the pulse Pf is changed, the level of the output pulse Po is once set to zero (or a level in the proximity of zero) such that immediately after the level inversion of the polarity pulse Pp or the frequency change of the pulse Pf, the level of the output pulse Po gradually increases. In consequence, in an operation in which the level of the output pulse Po gradually increases immediately after the polarity inversion of the polarity pulse Pp or the frequency change of the pulse Pf, it is possible to prevent an output pulse with a high level from being produced when the frequency of the output pulse is changed or when the signal causing an inversion of the polarity thereof is outputted (namely, to prevent the level of the output pulse from being kept remained at a level immediately before the polarity inversion or the frequency change), which has been the case of the prior art technology. Consequently, a feeling of a great electric shock is not caused on the human body, which leads to a considerably satisfactory feeling of electric shock.

The level to which the output pulse Po is set after the polarity inversion or the frequency change may be a level where the absolute value of the level of the pulse Po is equal to or is different from that of the level before the polarity inversion or the frequency change. For example, as shown in the second embodiment, the level may be determined according to the frequency.

In FIGS. 1 and 2, when the frequency is varied, it is naturally possible, as shown in the third embodiment that the level of the output pulse is once reduced to zero or to a level in the neighborhood of zero so as to thereafter gradually increase the level of the output pulse.

As described above, according to the present invention, a transcutaneous electric nerve stimulater capable of changing the frequency of the output pulse or capable of inverting the pulse polarity includes output level control means in which the output level of the output pulse is lowered to zero or to a level in the proximity of zero immediately before the frequency of the pulse is changed or the pulse polarity is inverted and in which immediately after the frequency of the pulse is changed or the pulse polarity is inverted, the level of the pulse is gradually increased up to a level immediately before the frequency change or the plarity inversion or to an appropriate level. In consequence, even when the frequency or the polarity of the output pulse is altered, a feeling of a great electric shock is not caused on the human body and a satisfactory feeling of electric shock is developed. As a result, an uncomfortable feeling of electric shock is prevented from being given to the patient and hence the operability of the transcutaneous electric nerve stimulater is improved.

While particular embodiments of the invention have been shown and described, it will be obvious to those skilled in the art that various changes and modifications may be made without departing from the present invention in its broader aspects.

We claim:

1. A transcutaneous electric nerve stimulater comprising:
   pulse generate means for generating an output pulse of which a frequency varies with a lapse of time; and
   pulse width control means for increasing a pulse width of the output pulse when the frequency becomes smaller and for reducing the pulse width when the frequency becomes greater.

2. A transcutaneous electric nerve stimulater according to claim 1 further including pulse amplitude control means for increasing a pulse amplitude of the output pulse when the frequency becomes smaller and for reducing the pulse amplitude when the frequency becomes greater.

3. A transcutaneous electric nerve stimulater according to claim 1 further including output level control means for decreasing a level of the output pulse to zero or to a level in the neighborhood of zero immediately before the frequency of the output pulse is changed and for gradually increasing the output level of the output pulse up to a predetermined level immediately after the frequency of the output pulse is changed.

4. A transcutaneous electric nerve stimulater comprising:
   pulse generate means for generating an output pulse of which a frequency varies with a lapse of time; and
   pulse amplitude control means for increasing a pulse amplitude of the output pulse when the frequency becomes smaller and for decreasing the pulse amplitude when the frequency becomes greater.

5. A transcutaneous electric nerve stimulater according to claim 4 further including output level control means for decreasing a level of the output pulse to zero or to a level in the neighborhood of zero immediately before the frequency of the output pulse is changed and for gradually increasing the output level of the output pulse up to a predetermined level immediately after the frequency of theoutput pulse is changed.

6. A transcutaneous electric nerve stimulater comprising:
output pulse state change means for increasing and for decreasing a frequency of an output pulse or for inverting a polarity of the output pulse; and
output level control means for decreasing an output level of the output pulse to zero or to a level in the neighborhood of zero immediately before the frequency of the output pulse is changed or the polarity of the output pulse is inverted and for gradually increasing the output level of the output pulse up to a predetermined level immediately after the frequency of the output pulse is changed or the polarity thereof is inverted.

7. A transcutaneous electric nerve stimulater according to claim 6 further including pulse width control means for increasing a pulse width of the output pulse when the frequency becomes smaller and for reducing the pulse width when the frequency becomes greater.

8. A transcutaneous electric nerve stimulater according to claim 6 further including pulse amplitude control means for increasing a pulse amplitude of the output pulse when the frequency becomes smaller and for reducing the pulse amplitude when the frequency becomes greater.

* * * * *